(12) United States Patent
Andersson

(10) Patent No.: US 7,867,753 B2
(45) Date of Patent: Jan. 11, 2011

(54) METHOD AND DEVICE FOR THE CHARACTERIZATION OF INTERACTIONS BETWEEN DIFFERENT SPECIES

(75) Inventor: Karl Andersson, Uppsala (SE)

(73) Assignee: Ridgeview Instruments AB, Uppsala (SE)

( * ) Notice: Subject to any disclaimer, the term of this patent is extended or adjusted under 35 U.S.C. 154(b) by 169 days.

(21) Appl. No.: 10/588,011

(22) PCT Filed: Feb. 16, 2005

(86) PCT No.: PCT/SE2005/000203

§ 371 (c)(1),
(2), (4) Date: Sep. 6, 2006

(87) PCT Pub. No.: WO2005/080967

PCT Pub. Date: Sep. 1, 2005

(65) Prior Publication Data

US 2007/0160979 A1    Jul. 12, 2007

(30) Foreign Application Priority Data

Feb. 20, 2004   (SE) .................................. 0400403

(51) Int. Cl.
*C12M 1/34*   (2006.01)
(52) U.S. Cl. .................................. 435/287.1
(58) Field of Classification Search ............. 435/287.1, 435/287.3, 88.3, 288.7, 4; 436/518; 422/50, 422/58, 67
See application file for complete search history.

(56) References Cited

U.S. PATENT DOCUMENTS

| 4,479,720 | A | | 10/1984 | Mochida et al. |
| 4,829,009 | A | * | 5/1989 | Graves ........................ 436/518 |
| 5,281,540 | A | * | 1/1994 | Merkh et al. ................. 436/530 |
| 6,444,461 | B1 | * | 9/2002 | Knapp et al. ............. 435/283.1 |
| 2003/0224457 | A1 | | 12/2003 | Hurt et al. |
| 2004/0023293 | A1 | | 2/2004 | Kreimer et al. |
| 2004/0137607 | A1 | * | 7/2004 | Tanaami et al. .......... 435/287.2 |
| 2004/0181343 | A1 | * | 9/2004 | Wigstrom et al. ............. 702/19 |

FOREIGN PATENT DOCUMENTS

WO   WO 02/40634   5/2002

* cited by examiner

Primary Examiner—Ann Y Lam
(74) Attorney, Agent, or Firm—Young & Thompson

(57) ABSTRACT

A device detects interactions between species in liquid and species on a solid support. It includes a solid support (11), a mechanism (16) for temporarily reducing the amount of a liquid to which the support is exposed, a detector (12) capable of detecting an interaction between species attached to the solid support, and species contained in the liquid. Also described is a method including attaching a first species on a solid support, exposing the first species to a liquid containing a second species, performing a measurement, capable of detecting an interaction between the first and the second species, and a reference measurement. The liquid is temporarily removed during the measurement.

10 Claims, 7 Drawing Sheets

METHOD AND DEVICE FOR THE CHARACTERIZATION OF INTERACTIONS BETWEEN DIFFERENT SPECIES

FIELD OF INVENTION

The present invention relates to the field of characterization of how different species interact with each other. More in particular, it relates to a method where one or more of the species are attached to a solid support and the other species are put in a liquid that is contacting the solid support. Even more in particular, it relates to the interaction of species of biological or chemical origin, e.g. cells, proteins, DNA, RNA, tissue, synthesized chemical compounds and the like.

BACKGROUND OF THE INVENTION

Interactions between different species are important in living organism and in industrial systems. The immune system is a first example, where antibodies in the bloodstream interact with pathogens and thereby guide natural killer cells to the pathogen. Therapeutic drugs is a second example, where a drug may interact with an enzyme in a way that inhibit the enzyme activity. A third example is detection of diseases in humans or animal, by contacting a sample from the human or animal with a liquid containing a species that interacts specifically with the pathogen causing the disease. If the species remains on the sample after a wash step, the sample is carrying the pathogen causing the disease. Exactly the same method can be used to detect contamination in food stuff. This means that methods and devices for characterization of interactions between species are important not only for research and diagnostics in biology and medicine, but also in quality control and characterization assays in a variety of fields.

There are many known methods for characterizing the interaction between two or more species. One common method is to attach one species to a solid support and add a second bifunctional species dissolved in liquid. The bifunctional species should (a) have a property that is easily detectable (e.g. be radioactive or have a fluorescent moiety attached to it) and (b) interact with the species that is attached to the solid support. The liquid is brought into contact with the solid support, sometimes followed by a wash of the solid support in a liquid without the bifunctional species. If the bifunctional species interacts stably with the species on the solid support it will accumulate on the solid support and remain there after a wash. Presence of the bifunctional species can then be detected. Another, more complicated method that has been widely used for the characterization of interactions is enzyme linked immunosorbent assay (ELISA).

The present invention aims at facilitating the characterization of how species interact with each other. The method is particularly suitable when one of the species is large (in a molecular context), e.g. if one of the species is cells or bacteria.

CLOSEST PRIOR ART

Pierce Biotechnology Inc (Rockford, Ill., United States of America) manufactures and sells a microplate where the bottom of each well has up to 16 defined areas where antibodies that recognize specific proteins are attached (Searchlight™). When a liquid sample is put in a well the specific proteins are bound to the different areas on the bottom of the well. The detection of the different proteins is mediated by secondary antibodies, one for each specific protein, labeled with a moiety that emits light. A camera is then used to quantify the light intensity, which is related to the specific protein concentration, on each defined area. This method is presently limited to proteins and does not explicitly use one defined area for reference purposes. A detailed description of the Searchlight™ method may be found in an article by M D Moody, S W Van Arsdell, K P Murphy, S F Orencole and C Burns (Biotechniques (31(1):186-90, 192-4, July 2001) which is incorporated by reference herein.

Biacore AB (Uppsala, Sweden) manufactures an optical biosensor (Biacore®3000) that has a solid support with 4 defined areas where different species can be attached. Liquid samples are injected onto the solid support. If a species present in the liquid is binding to the species attached to the solid support, the refractive index close to the solid support will change. The optical detection system monitors refractive index close to the solid support in real time. When operating this instrument, it is recommended to use one of the defined areas for reference purposes. The liquid that is in contact with the solid support is however not stirred, instead there is a continuous flow of liquid over the solid support. Although the Biacore®3000 was primarily designed to monitor interactions between proteins, interactions between cells and proteins have been monitored. A detailed discussion of the technical aspects of the BIACORE instrument may be found in U.S. Pat. No. 5,313,264 which is incorporated by reference herein.

An optical biodisc and an accompanying disc reading apparatus has been described by S N Hurt, J F Gordon and K R McIntyre (US Patent Application Publication No. US2003/0224457), which is incorporated by reference herein. The biodisc is an essentially flat plastic disc which includes radial oriented channels with inlet and outlet ports. In each channel there is a plurality of target zones onto which different antibodies are immobilized. Some target zones have antibodies recognizing antigens on cells that are specific for a unique blood type. Other target zones serve as negative or positive controls. A cell suspension, e.g. a blood sample, is injected into a channel. Certain cells in the suspension may then bind to the target zone carrying antibodies specific for the blood type of the patient. Next, the disc is rotated to move all unbound cells away from the target zones. In a last step, the blood type of the patient can be determined by optically detecting which target zones cells have bound to. This means that the biodisc measurement does not necessarily include a wash step, instead unbound cells are completely removed from the detection area by accelerated sedimentation caused by rotating the disc at a high speed.

SUMMARY OF THE INVENTION

The object of the present invention is to facilitate the characterization of how different species interact with each other. In a first aspect the invention provides a device for the characterization of interaction between species. This device is defined in claim 1.

In a further aspect, the invention provides a method for the characterization of how different species interact with each other. The method according to the invention is defined in claim 6.

The invention in a preferred embodiment has four characteristic features.

A solid support with at least two defined areas, namely one for a target and at least one for reference purposes. However, several different targets can be provided in separate defined areas. A liquid containing a dissolved ligand is in contact with the solid support to enable an interaction between target and ligand.

A detector is arranged so as to be able to detect and quantify the presence of the ligand near the defined areas.

Preferably stirring of the liquid in contact with the solid support is provided for.

An essential feature is provision of means for at least temporarily reducing the amount of liquid at a defined area during detection.

When quantifying the amount of ligand near the reference area, unbound ligand present in the liquid remaining near the defined area, ligand unspecifically bound to the reference area, and background signal not related to the ligand will contribute to the signal. When quantifying the amount of ligand near a target area, ligand bound to the species attached to the solid support will be an additional source of signal. Thus, the detected amount of ligand bound to the target can then be corrected for the background signal by subtraction of the signal from the reference area.

Since the signal associated with unbound ligand in the liquid can be much greater than the signal from ligand bound to the solid support, it is beneficial to reduce the amount of liquid during the measurement of ligand near a defined area. It is however not necessary to remove the liquid completely. There are two reasons for stirring the liquid. Firstly, the liquid will be homogenous in the container and secondly, the time required to reach equilibrium will not be increased due to slow diffusion of the ligand in the liquid.

BRIEF DESCRIPTION OF THE DRAWINGS

The present invention will be disclosed in closer detail in the description and example below, with reference to the accompanying drawing, in which.

DETAILED DESCRIPTION OF THE INVENTION

Figure 1:
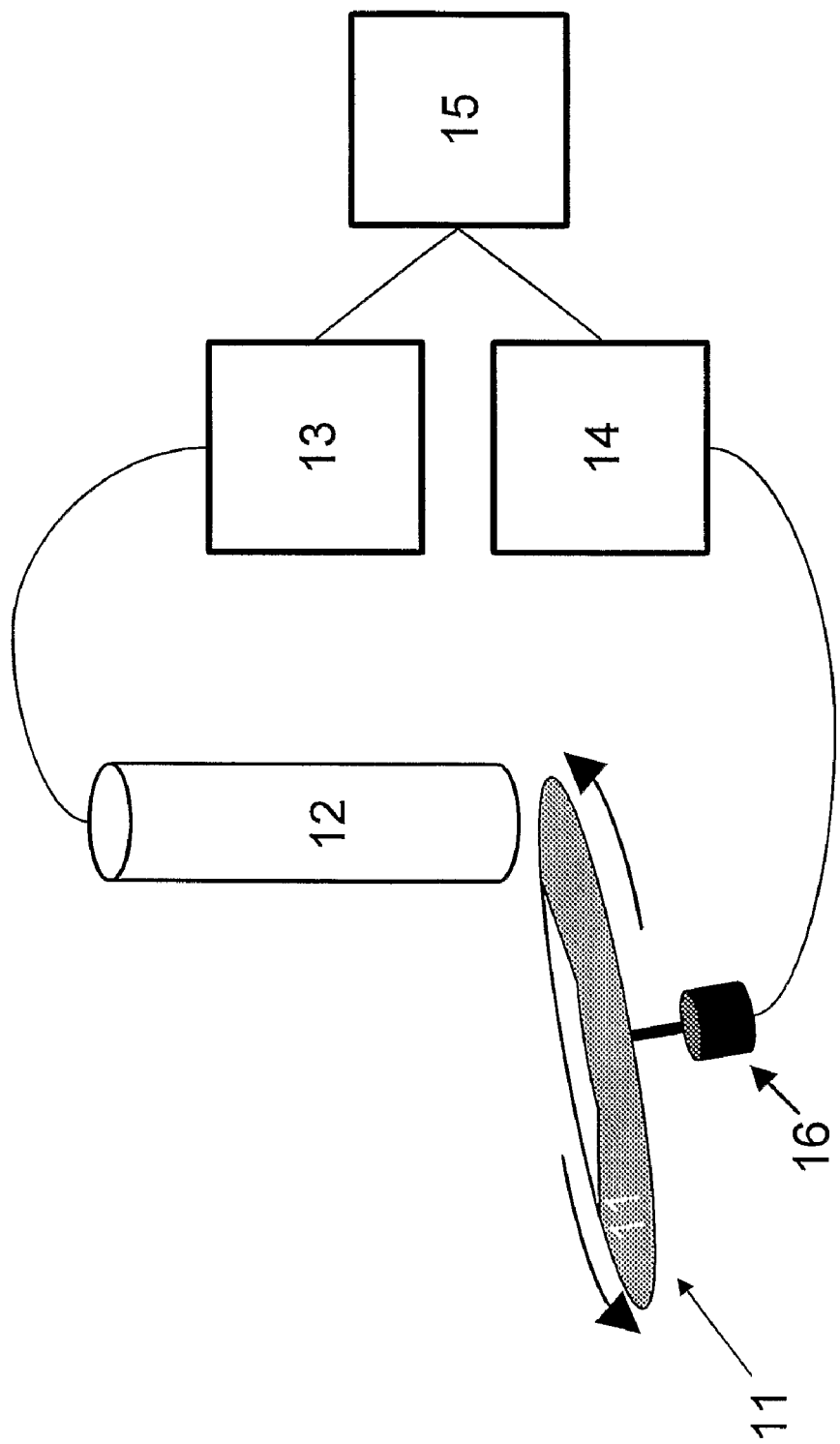
FIG. 1 shows a schematic of one possible instrument design.

For the purpose of the present application, and for clarity, a species that is attached to the solid support is denoted "target" and a species present in a liquid is denoted "ligand". Possible species (i.e. targets and ligands) include, but are not limited to, tissue samples, cells, bacteria, viruses, solid particles, macromolecules (e.g. proteins, DNA, RNA) and other chemical compounds. Preferred ligands include macromolecules (e.g. proteins, DNA, RNA), other chemical compounds and any species that can be dissolved in a liquid.

The present invention aims at improving the accuracy and precision of the characterization of interactions between different species. Another aim is to reduce the labor time required for performing a characterization.

Generally, a device according to the present invention for detecting interactions between species attached to a support (targets) and species in a liquid (ligands), when said support and said liquid are brought into contact; comprises: a solid support (11) on which a first species can be attached in one or more non-overlapping defined areas thereon; a detector (12) capable of detecting an interaction between said species attached to the solid support, and said species contained in said liquid. The device is characterized by a mechanism (16) adapted for temporarily reducing, in a defined area of said support, the amount of liquid with which said support is brought into contact in the course of a detection; and at least one of the defined areas do not have a species of interest attached, so as to form a reference area for the detection.

The second species can preferably be present in the liquid as a dissolved molecule or a dissolved complex of molecules with a total molecular weight less than 1000000 g/mole.

Preferably the solid support is an essentially flat dish capable of holding a liquid confined within its boundaries, such as a Petri dish, although any other kind of receptacle or vessel capable of confining liquid is possible.

In order to remove liquid, the invention provides in one embodiment an aspirating device for aspirating liquid from said support before measurement, and for returning liquid to the support after measurement.

Preferably, the detector 12 is a scintillation detector, although many other types of detectors are possible, see below. There is further provided an electronic counter device 13 for counting the impulses from the detector 12, and a control unit for adjusting and reporting the angular position of the support 11, and a computer 15 for synchronizing scintillation counter output from the counter 13 and the angular position of the cell dish support from the control unit 14.

The method according to the invention, which is suitably carried out with a device such as the one described, comprises attaching a first species on a defined portion of a solid support. Then said first species (target) is exposed to a liquid containing a second species (ligand), so as to cover the defined portion of the solid support. A measurement is performed, capable of detecting an interaction between said first and said second species. According to the invention the amount of liquid covering the defined portion of the support is temporarily reduced prior to performing said measurement. A reference measurement is performed on a different portion of the solid support where no interaction takes place, said portion defining a reference area.

The temporary reduction of liquid comprises a reduction of the amount of liquid near at least one of said defined areas without changing the total amount of liquid in contact with said solid support.

Suitably, a difference between target and reference measurements is calculated.

The sequence of steps of exposing, measuring and reducing the amount of liquid is preferably repeated, and the concentration of said ligand is increased by a finite amount before said sequence of steps is repeated.

In a preferred embodiment, the interactions on all defined areas are detected within 1 minute, and the detection of all interactions are preferably repeated without interruption during at least 15 minutes in order determine the progress of the interaction over time.

In a further preferred embodiment of the method, the reduction of the amount of liquid is achieved by orienting the support at an angle that deviates from the horizontal to provide an elevated part and a lower part of said support, such that the elevated part will be covered by less liquid than the lower part, and wherein the support is rotated at a predetermined speed of rotation.

Preferably the first species is selected from tissues, cells, bacteria, virus particles, and the second species present in the liquid is a dissolved molecule or a dissolved complex of molecules with a total molecular weight less than 1000000 g/mole.

According to one embodiment of the invention, a device comprising four main characteristics is used for the characterization of interactions between ligands and targets. Namely, on one single solid support two or more areas are defined, where at least one area is reserved for attaching a target (also referred to as an active area) and at least one area is reserved for reference purposes. A reference area either has nothing attached to it or has an irrelevant target attached to it. Furthermore, liquid containing a ligand is in contact with the solid support. There is also a detection system able to detect presence and quantity of the ligand on each area. There is a mechanism for stirring the liquid present on the solid support. Finally, there is a mechanism that ensures that the amount of liquid present close to a defined area is temporarily reduced during detection.

Since the same liquid contacts the active area (target) and the reference area and separate detection of presence of ligand on the active and reference areas, respectively, is possible, a background correction is obtained by subtracting the detector output for the reference area from the active area. Also, since the liquid is stirred, the time required to reach equilibrium will decrease compared to when the solid support and liquid is left still.

Commonly used methods for characterization of interactions between targets and ligands often include a wash step. The purpose is to remove all ligand that has not bound to the target, since presence of unbound ligand may be detected. Advantageously, in the present invention, a wash step is not necessary due to the use of a reference area and due to the temporary reduction of liquid during detection. Since the presence of ligand is quantified at all areas in short time and since the liquid containing ligand is temporarily reduced, the reference area will mimic the active area in terms of radiation associated with unbound ligand in the remaining liquid close to the area and background radiation. However, a wash step can increase the sensitivity in cases where a very high concentration of ligand is present in the liquid.

Since a wash step is not required, liquid containing ligand can be reused throughout a characterization. This is of particular interest when the ligand is expensive. In this case, a liquid with low concentration of ligand is put into contact with the solid support. After characterization of this first concentration a small aliquot of highly concentrated ligand is added. The total concentration of ligand then increases to a second level, and the binding is characterized. This process is repeated until the desired concentrations have been characterized.

The solid support is typically a container. In this container two or more defined areas are present. Liquid put in the container contacts all defined areas. At least one defined area is always reserved for reference purposes. This makes it possible to characterize the interaction of one ligand with several targets simultaneously. Another possibility is to use a detection system that can distinguish different ligands, e.g. by attaching different fluorescence dyes on the different ligands and detecting the light intensity at the different characteristic emission wavelengths corresponding to the defined dyes. With this setup, several ligands can be put in one liquid and binding of all ligands to one or more targets can be characterized simultaneously.

The attachment of target on the defined areas can be performed in a variety of ways. Cells could be grown directly on a defined area. The defined areas could be coated with a protein known to enhance attachment of cells. The defined areas could be coated with a protein known to bind a specific molecule which is used for attachment of the target. One such protein is streptavidin which binds biotin strongly. A biotinylated target (e.g. biotinylated DNA) could then be conveniently attached as target to the defined area. The surface of the defined areas could be chemically modified to make possible covalent attachment of a target. Passive adsorption of target directly onto the defined area is also possible. The surface of the defined areas is not necessarily solid and flat. Porous surfaces or surfaces with biopolymers attached (e.g. polyethylene glycol or dextran) could be advantageous due to increased target density making a higher signal possible.

The defined areas on the solid support do not need to be explicitly marked. When growing cells are used as target, a drop of cells can be put on the solid support, leaving the majority of the solid support clean for reference purposes. When the cells have sedimented and started to attach to the solid support more liquid (without cells) can be carefully added to the solid support to prevent the cells from drying. It is also possible to physically divide the solid support into defined areas by use of low ridges or the like. The ridges should be high enough to prevent liquid from reaching other defined areas during attachment of target, but low enough to let liquid contact all defined areas simultaneously during measurement.

This method can use several different detection principles. Two different types of detector set-ups are possible: Detectors that are in physical contact with the solid support and detectors that are not in physical contact with the solid support. Detector principles that do require physical contact with the solid support include (but are not limited to) electrochemical detection of ligand, refractometric detection of ligand. Detector principles that do not require physical contact with the solid support include (but are not limited to) detection of radioactivity, detection of emitted light (e.g. using fluorescence or chemoluminence), spectrophotometric detection, just to mention a few. The detection system used in this method is time resolved. This means that detection of a defined area is repeated at least every tenth minute, preferably every 20-60 seconds, even more preferably every 0.1-20 seconds. The time-resolved measurement makes it possible to monitor the rate of ligand binding to the target, also known as the kinetics of the interaction.

A mechanism that temporarily decreases the amount of liquid in the vicinity of the defined area during detection is beneficial but not necessary. The method relies on differential measurements (i.e. signal from active area minus signal from reference area) and as such it should not, in theory, be affected by excess of liquid present in the vicinity of the defined area during detection. In practice, performance may increase when such excess liquid is temporarily removed. The problem is that for some detection principles, e.g. detection of radioactivity, the amount of ligand present in a volume close to the detector will be detected. This volume includes the defined area and the liquid present near the defined area. The amount of unbound ligand present in the liquid will often be much larger than the amount of ligand bound to the target, which means that the detector will register almost the same amount of radioactivity during detection of an active area and a reference area. The resolution for such differential measurements can sometimes be low. This problem can be overcome by temporarily reducing the amount of liquid covering the solid support during detection. The liquid remaining on the defined areas might then contain enough ligand to be detected, but the magnitude of the liquid-associated signal will be comparable to the magnitude of the signal associated with the defined area. The currently preferred method avoid detrimental impact of signal from unbound ligand present in the liquid is to completely remove the liquid. The most common method used to remove the liquid containing ligand is to wash the solid support with a suitable liquid devoid of ligand. Another less common but possible method, applicable when the ligand is a particle or a cell, is to centrifuge the solid support and thereby move the unbound ligands to the radially most distant part of the solid support (as described in US Patent Application Publication number US2003/0224457, which is incorporated by reference herein). There is however a drawback with removing all unbound ligands. The interaction of ligand with target is typically a reversible process. A simple and common model for biomolecular interactions is described by the following equation:

$$K_D = \frac{[T] \cdot [L]}{[TL]} \quad (1)$$

where $K_D$ is the equilibrium dissociation constant for the target-ligand interaction, [T] is the concentration of unbound target, [L] is the concentration of unbound ligand, and [TL] is the concentration of target-ligand complexes. When the solid support is contacted with liquid containing ligand, target-ligand complexes will be formed until [T], [L], and [TL] satisfies Equation 1. The time required to reach equilibrium varies from a few seconds to a many hours. The reverse process will start if all unbound ligands are removed, i.e. [L] is suddenly set to zero. In order to re-establish equilibrium, target-ligand complexes will spontaneously break. Thus, when removing unbound ligand prior to measurement, the number of target-ligand complexes will decrease during the measurement and negatively impact the measurement. This problem has been discussed in the literature, for example in an article by M Wadhwa et al. (see section 2.1.1 in "Strategies for detection, measurement and characterization of unwanted antibodies induced by therapeutic biologicals", M Wadhwa, C Bird, P Dilger, R Gaines-Das, and R Thorpe, Journal of Immunological Methods, 278:1-17, 2003), which is incorporated by reference herein.

By instead temporarily reducing the amount of liquid containing ligand near the defined area on the solid support during measurement, there will at the most be a minor change in unbound ligand concentration leading to at the most a minor adjustment of [T], [L], and [TL]. Thus, a more accurate measurement of the number of target-ligand complexes is anticipated, in particular for interactions that adjust to equilibrium within a few seconds. On the other hand, the liquid remaining near the defined area where the measurement is performed will contain unbound ligand which contributes to the total signal. In summary, prior art methods have removed the unbound ligand and have accepted a continuous breakdown of target-ligand complexes. The method of this invention prevents target-ligand complex breakdown from occurring, but has to handle the presence of liquid containing ligand near the defined area during measurement.

One possible method to reduce the amount of liquid near a defined area on the solid support is to use a circular solid support (e.g. a cell dish) and put defined areas along the perimeter of the solid support. If such a solid support is placed on a rotating disk that is mounted with a slight slope it becomes possible to position a defined area at the highest position during detection. Liquid present on the solid support will accumulate in the lower end of the solid support and will not severely impact the quantification of ligand on the defined area. Another possible method for temporarily moving liquid on the solid support is to tilt the solid support during detection. If the defined areas are put in one end of a solid support and this end is elevated during detection, liquid present on the solid support will accumulate in the other end and make a more reliable detection possible. A third possible method is to use a pump that aspirates the liquid on the solid support during detection, and dispenses the liquid back onto the solid support afterwards. It is notable that all these methods also provide a stirring of the liquid present on the solid support. The amount of liquid that remains on the defined area during detection should be less than 10%, preferably less that 5% and even more preferable less than 1% of the amount of liquid present in the vicinity of the defined area when the solid support is positioned horizontally in rest. This could be measured using a solid support without any target attached to the defined areas and compare the signal from a defined area in horizontal position with the signal from the same defined area in position for detection with the liquid temporarily removed. A sufficient reduction of liquid with ligand on the defined area can be defined in terms of background signal contribution. It is acceptable that liquid still present on the defined area during detection give a background signal that is at most ten times, and preferably at most two times, the expected signal originating from ligand bound to target. The acceptable amount of remaining liquid cannot easily be expressed in terms of percent removal, because the value depend many parameters (e.g. the concentration of the ligand, the affinity of the interaction and the initial volume of the liquid in the solid support). As a typical value, an interaction would be measurable when 0.1-1% of the liquid is still present on the defined area during detection if the affinity is approximately $1 \times 10^{-8}$ M, the ligand concentration in the range of $1 \times 10^{-9}$ M to $5 \times 10^{-9}$ M, the solid support is a Petri dish with a diameter of approximately 10 cm and the liquid volume is approximately 2 ml.

If stirring is not obtained from the method of temporarily removing liquid from the solid support, a stirring device is required. This could be a vibrating rod or a rotating propeller that is put in the liquid. Alternatively, the solid support could be moved repeatedly to induce movements in the liquid. Possible motions include gentle shaking and excentric rotation.

The physical structure of one embodiment of a device according to the invention is illustrated in FIG. 1. For this embodiment a radioactively labeled ligand is used, whereby the target will become radioactive when ligand binds thereto. The device comprises two key components.
  (i) a cell dish support that can be rotated slowly 11.
  (ii) a time-resolved scintillation counter 12 mounted such that it will detect interactions present only on a peripheral part of the cell dish.

A stepper motor 16 is connected to the cell dish support 11. The motor is controlled by an electronic device 14 that both can adjust the angular position and report the angular position of the cell dish support. The scintillation detector 12 is connected to an electronic device 13 that counts the number of impulses from the detector 12. The cell dish support is inclined and the scintillation counter is located at the highest point of the cell dish support. The scintillation counter is read with a high frequency to allow multiple activity measurements during one round. A computer 15 synchronizes scintillation counter output from 13 and the angular position of the cell dish support from 14 and generates an activity versus angular position curve.

The target, here human cancer cells, are grown only on a limited sector of the cell dish, as indicated in white in FIG. 1. A liquid containing the ligand, in this case a radioactively labeled protein, is added to the cell dish. It is known that the ligand binds to receptors present on the target cell surface. As the dish rotates, the activity of the dish bottom will be continuously monitored, sometimes an area with target cells, sometimes an area without target cells. If the ligand binds to the target cells, an increase of the radioactivity will be registered by the scintillation counter when the target cell sector of the cell dish passes the detector.

The four (main) features of the invention mentioned previously can be embodied as described below.

The solid support, i.e. the cell dish, has a limited area with target cells on. The remaining area of the cell dish is used for reference purposes. The detector is mounted in a peripheral part of the cell dish. When the cell dish rotates, the radioactivity is frequently registered. This makes it possible to plot degree of radioactivity (i.e. the amount of ligand) versus position on cell dish perimeter. The stirring is obtained by mounting the cell dish non-horizontally. When the cell dish rotates, the liquid will start to rotate but with a different speed than the cell dish. The temporary removal of liquid is also obtained by mounting the cell dish non-horizontally. The detector is mounted near the highest point of the cell dish which is the point where there is the least amount of liquid.

The following non-limiting examples of the invention will illustrate the principle behind it.

EXAMPLE 1

The instrument described above was tested with U343 cells grown on one quarter of a 10 cm circular cell-dish. The dish was rotated with a speed of approximately 6 rounds per minute. It is important to select a proper rotational speed for the dish. If the dish rotates too fast the liquid present in the dish will not have time to accumulate in the lower end of the dish yielding a poor temporary removal of liquid near the detector. If the rotation is too slow the measurements of the active area and the reference are too distant in time to justify a differential measurement. Rotational speeds proper for the instrument in this example range from approximately 1 round per minute to approximately 1 round per second. 2 ml of liquid containing increasing concentrations of EGF (Epidermal Growth Factor) labeled with $^{125}$I was added to the cell-dish. EGF is known to bind to the EGF receptor, and U343 cells are known to have high levels of EGF receptors on their surface. The radioactivity was measured at least 2 times per second giving approximately 20 measurements per round. Since EGF is known to bind to the cells, the measured radioactivity will be higher when the area of the cell-dish holding target cells passes by the detector compared to other times. This gives a continuous wave-like time series where the period is determined by the angular speed of the dish and the amplitude by the amount of EGF binding to the cells.

Figure 2A:
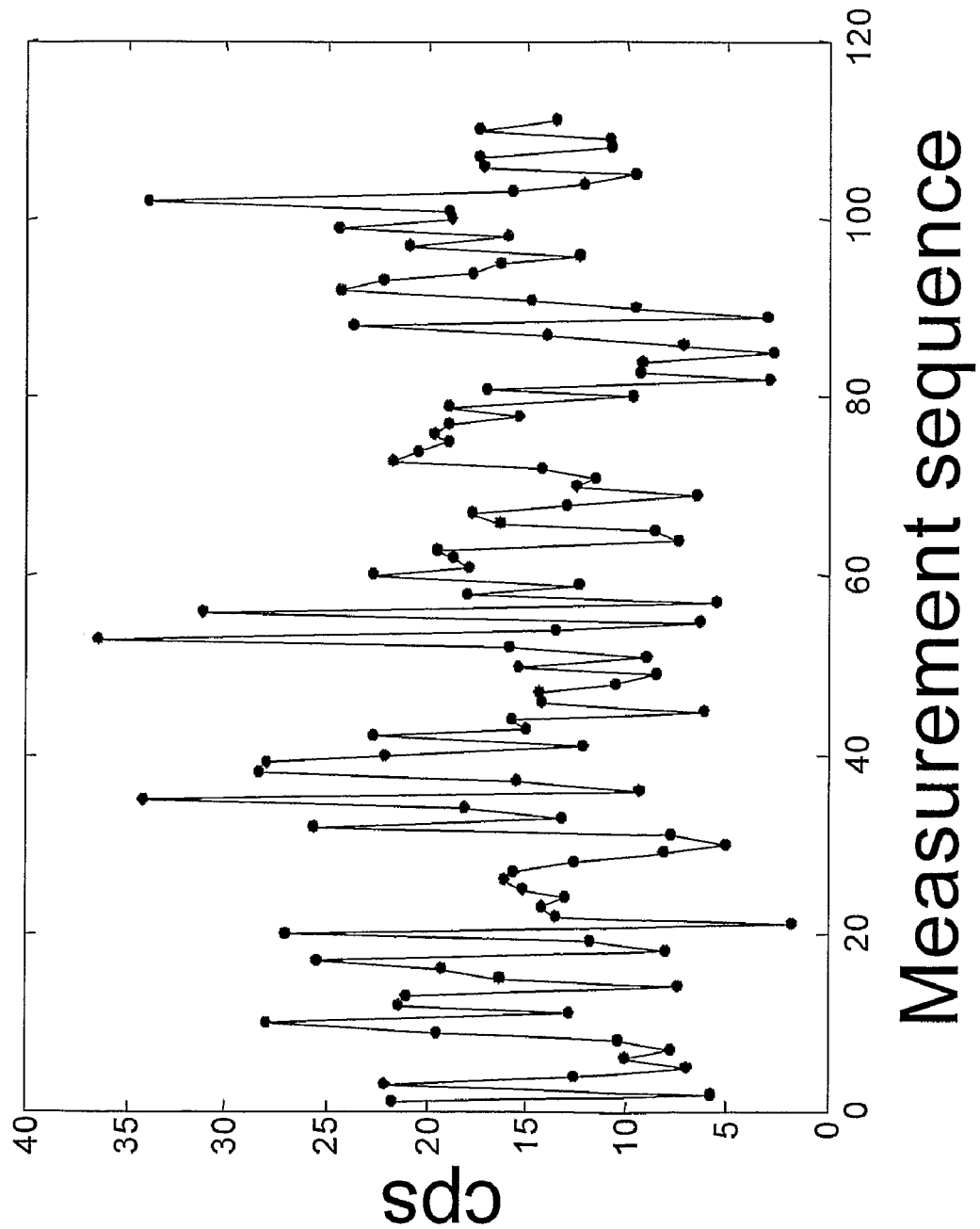
FIG. 2a shows data acquired with a very low concentration of the ligand.
Figure 2B:
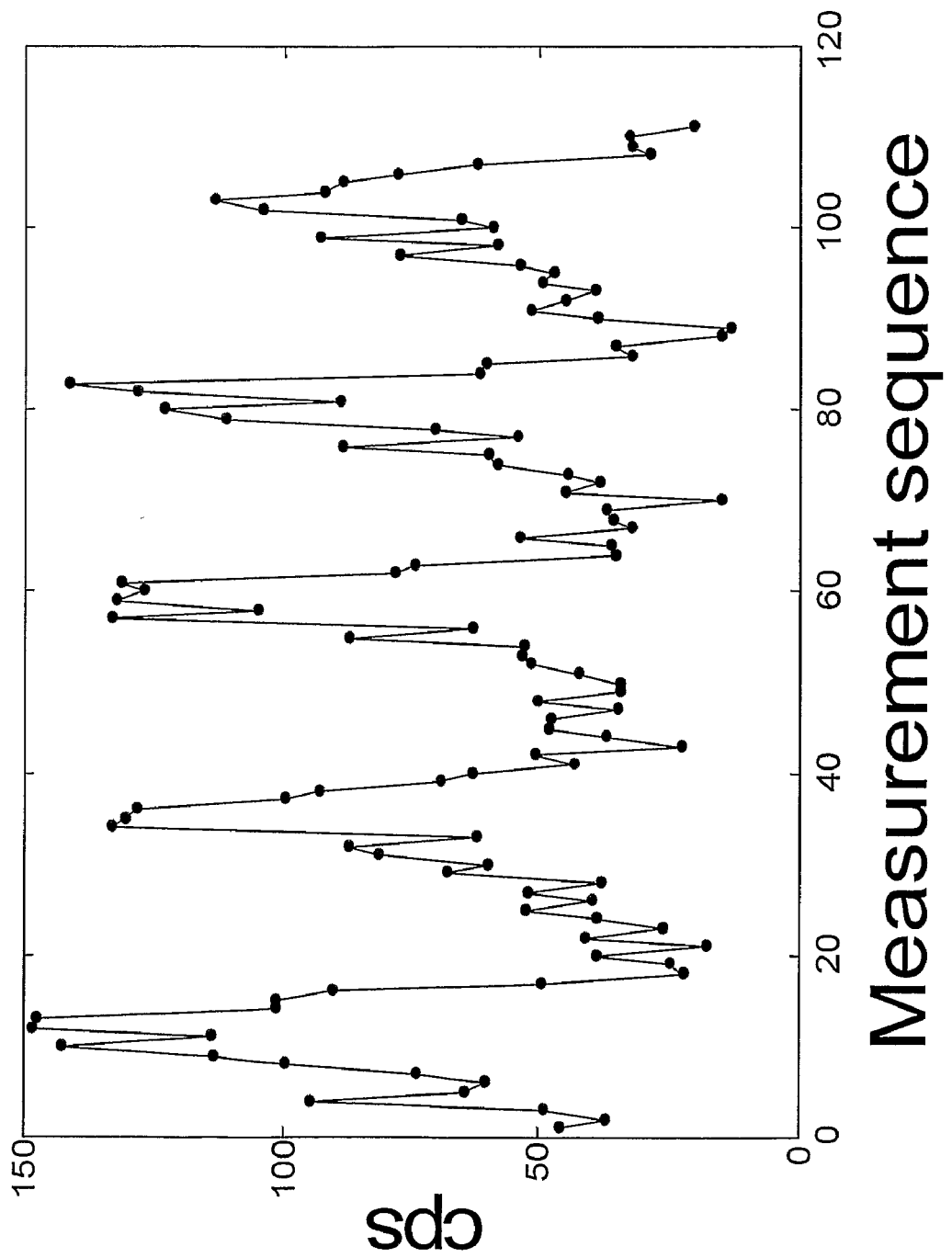
FIG. 2b shows data acquired with a high concentration of the ligand.
Figure 3A:
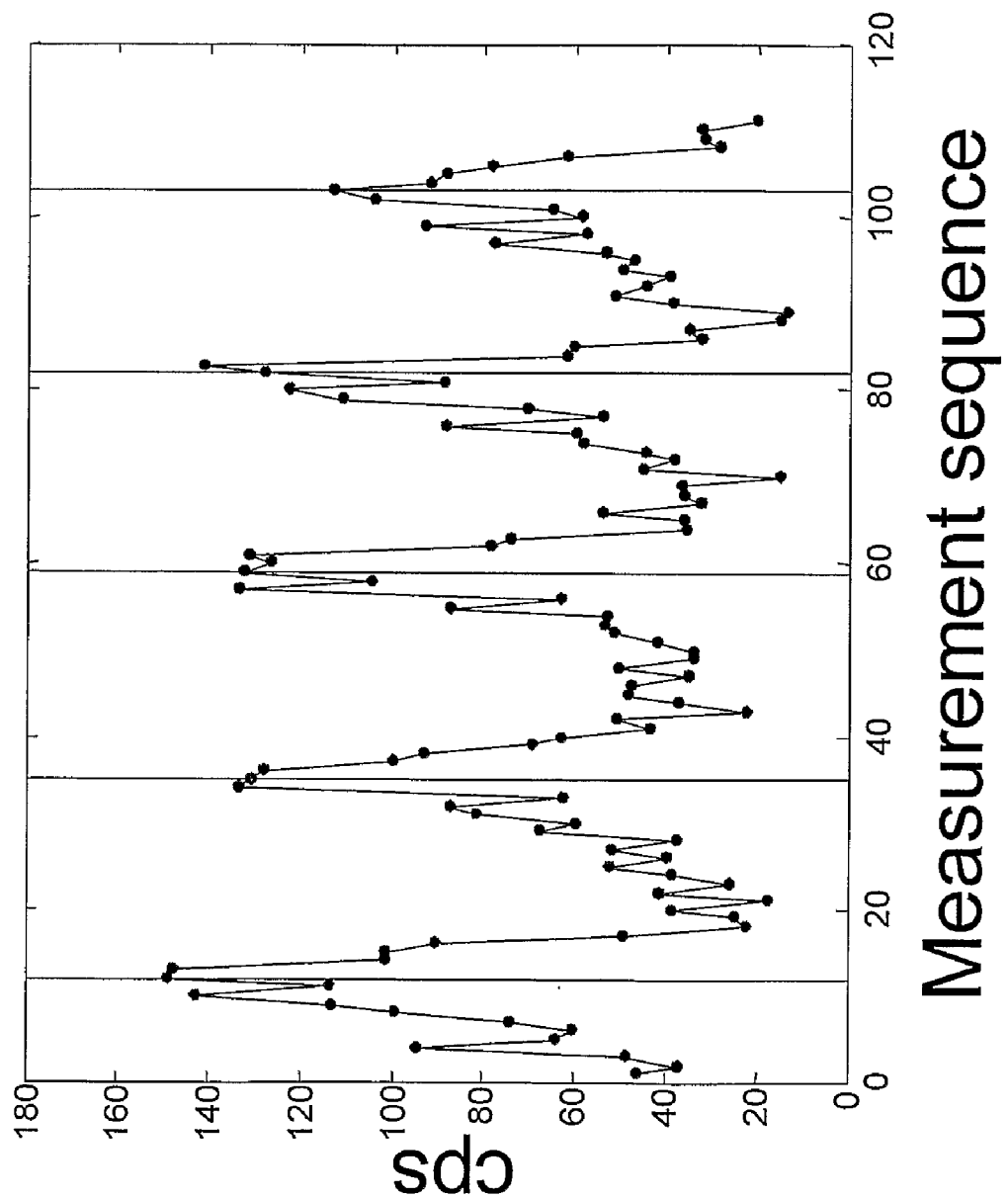
FIGS. 3a and 3b illustrates how the acquired data is processed prior to evaluation.
Figure 3B:
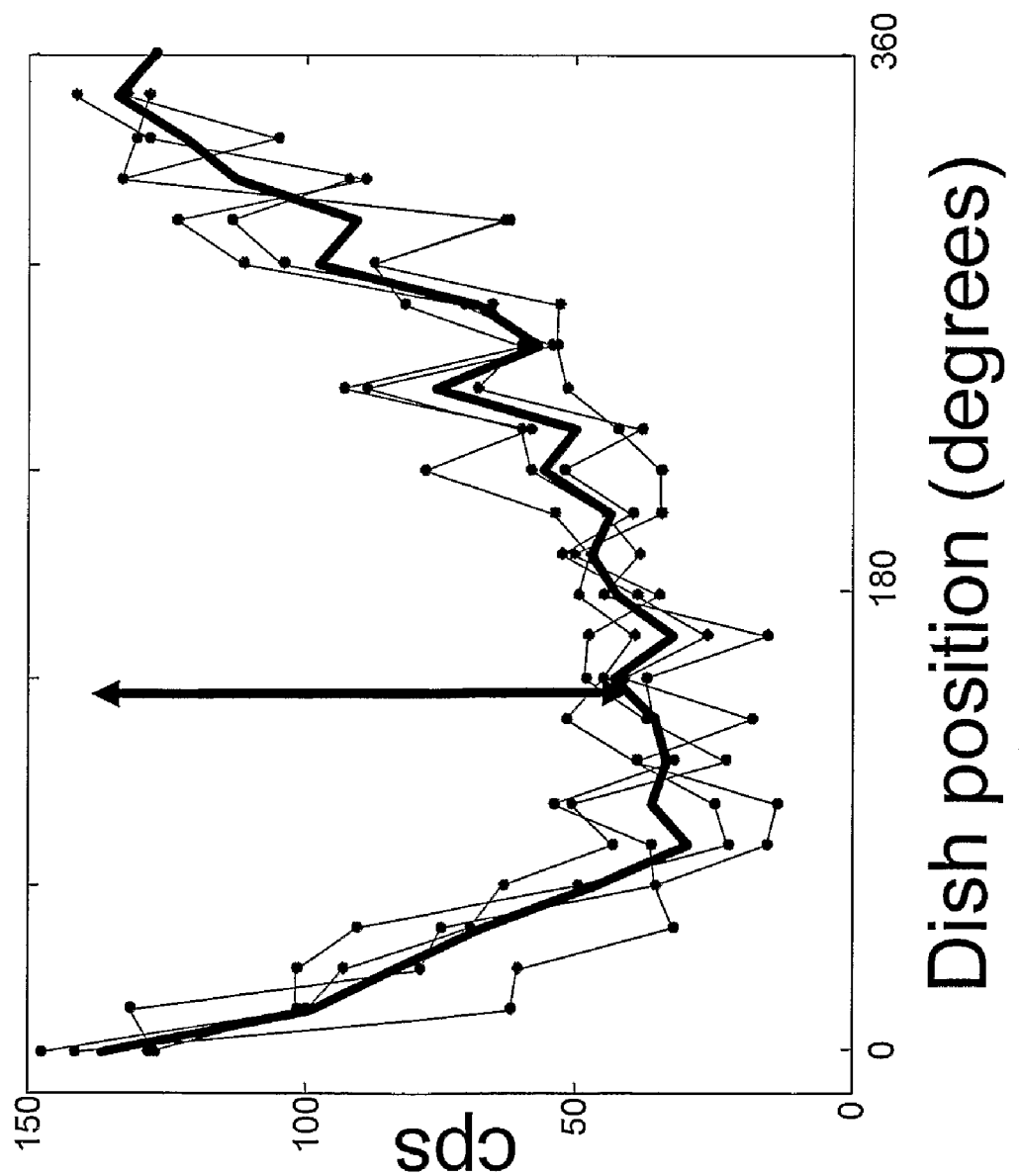

In FIG. 2, two time-series are plotted, one with a low concentration of EGF and one with a higher concentration. The y-axes in FIG. 2 have the unit counts per second (cps), i.e. the number of $^{125}$I decays per second. At the low concentration, there is no obvious pattern in the time series. This means that the amount of EGF bound to the target cells was very low. At the higher concentration, a clear wave-like pattern appears, proving that EGF is bound specifically to the part of the cell-dish where there actually are cells. In order to increase the precision a 3-6 minute long time-series was obtained for each concentration EGF. All peaks in the time-series were then identified, peak-to-peak fragments were cut, overlayed and averaged as outlined in FIG. 3. The amplitude of the thicker average line was used as signal for the measurement, as illustrated by the arrow.

In order to collect a binding curve for radiolabeled EGF binding to U343 cells, 8 different concentrations of radiolabeled EGF were added to one cell dish put in the instrument. The sequence of operation was:
1. Add 4 ml of medium+radiolabeled EGF. Rotate dish for 500 s.
2. Take a 200 ul aliquot of the medium+radiolabeled EGF liquid to make concentration determination possible.
3. Wash the cell dish with 4-8 ml medium (this step was omitted for the three lowest concentrations).
4. Add 4 ml of medium. Record the radioactivity (time resolved) during 500 s.
5. Repeat step 1-4 with increasing concentrations of radiolabeled EGF.

Figure 4:
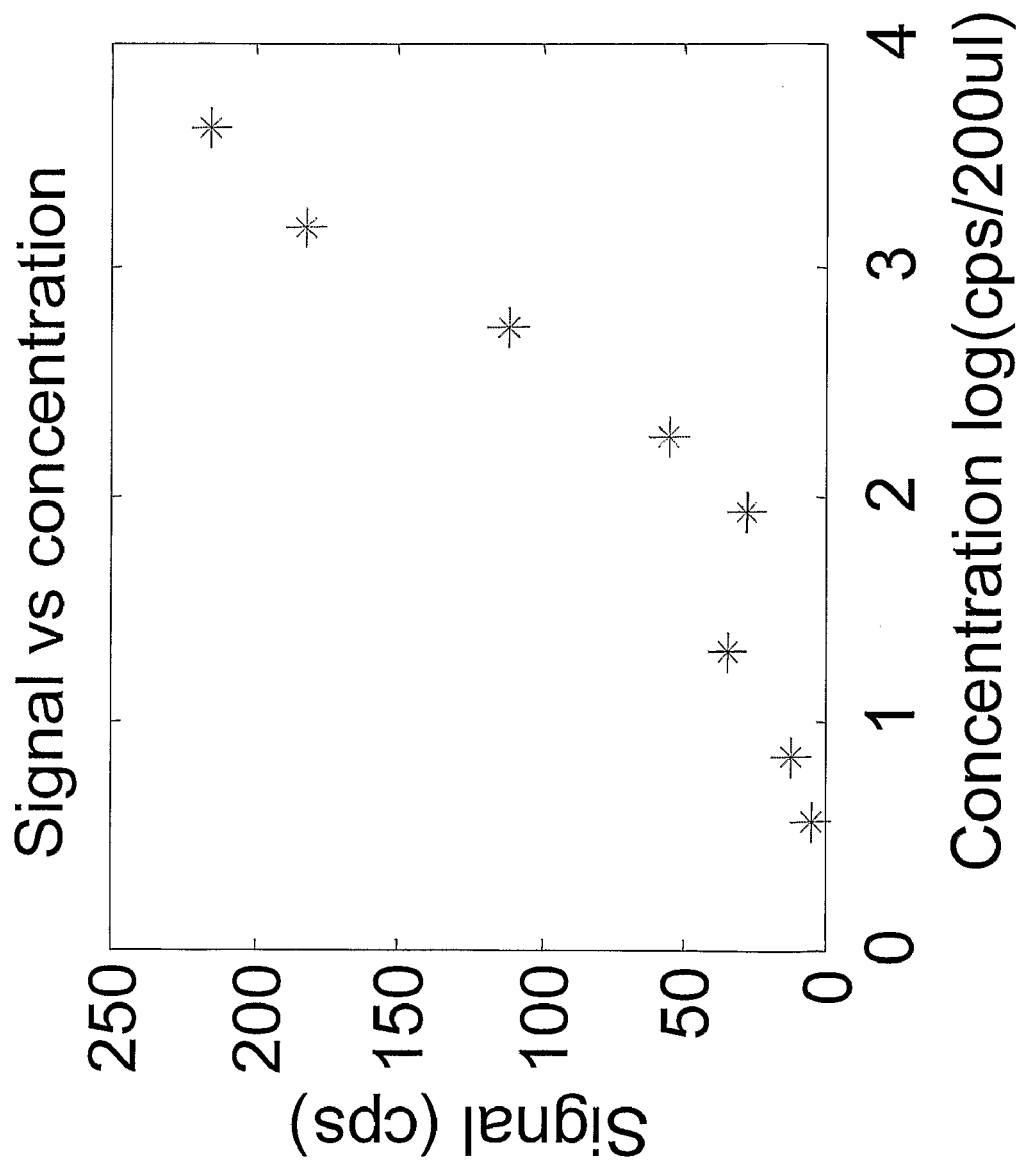
FIG. 4 shows how different concentrations of a ligand give rise to different signals.

The signal for each sample was determined as described above, by overlaying peak-to-peak fragments, averaging and extracting the wave amplitude. A signal versus concentration plot is found in FIG. 4. It clearly resembles the sigmoidal curve expected from a binding experiment. The first three samples were measured directly without a wash step (point 3 in the sequence of operation above), which explains the discontinuity between sample 3 and sample 4.

EXAMPLE 2

In a similar experiment, A431 cells were grown on a limited area on a 8 cm cell dish. A431 cells also have high levels of EGF receptor on the surface. The sequence of operation in this experiment was:
1. Add 2 ml of cell culture medium+radiolabeled EGF. Rotate dish for 700 s.
2. Continue to rotate the dish for another 200 s, but also record the radioactivity (time resolved).
3. Take a 200 ul aliquot of the medium+radiolabeled EGF liquid to make concentration determination possible.
4. Wash the cell dish with approximately 4 ml medium
5. Add 2 ml of medium. Record the radioactivity (time resolved) during 200 s.
6. Repeat step 1-5 with increasing concentrations of radiolabeled EGF.

Figure 5:
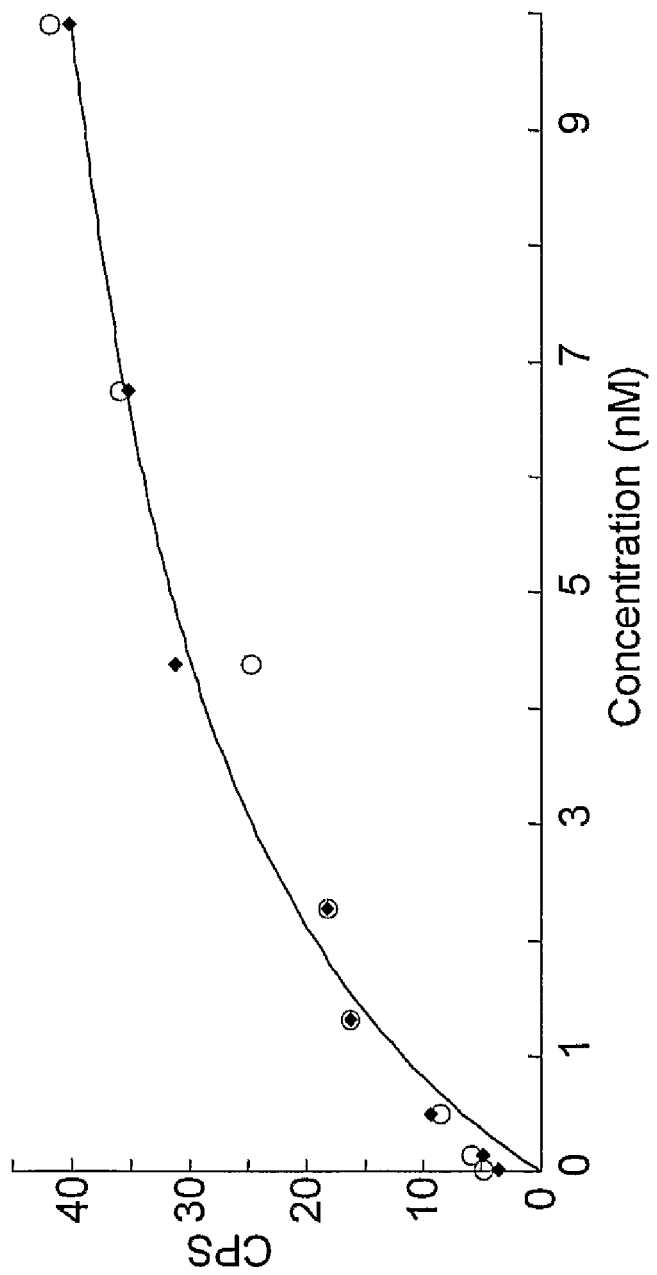
FIG. 5 shows how different concentrations of a ligand give rise to different signals obtained with and without a wash step, respectively.

The signals for each concentration before and after wash were derived as described above and are plotted in FIG. 5, where the diamonds corresponds to measurements before wash (step 2) and the circles corresponds to measurements after wash (step 5). Since the values measured before and after wash generally agree, the wash was not necessary for obtaining valid measurements. The affinity of the interaction could be determined by fitting Smax and KD in the equation $$S=Smax*conc/(KD+conc) \quad (2)$$

to the measured data. In equation 2, S is the measured signal for ligand concentration conc, Smax is the binding capacity of the targets in the defined area and KD is the affinity of the interaction. This procedure has been previously described by Karlsson R., Ståhlberg, R. 1995, Surface Plasmon Resonance Detection and Multispot Sensing for Direct Monitoring of Interactions Involving Low-Molecular-Weight Analytes and for Determination of Low Affinities, Anal. Biochem. 228: 274-280, which is incorporated by reference herein. The calculated affinity was KD=3.7 nM and the calculated binding capacity was 55 CPS. The calculated affinity is in fair agreement with values in the literature: Affinities for the EGF-EGF receptor interaction ranging from 0.3 nM to 7 nM have been reported, as summarized in table 1 in Sundberg A. L., A. Orlova, A. Bruskin, L. Gedda, J. Carlsson, E. Blomquist, H. Lundqvist, V. Tolmachev. 2003, [(111)In]Bz-DTPA-hEGF: Preparation and in vitro characterization of a potential antiglioblastoma targeting agent. Cancer Biother. Radiopharm. 18(4):643-54, which is incorporated by reference herein.

Although the invention has been described with regard to its preferred embodiment, which constitute the best mode currently known to the inventor, it should be understood that various changes and modifications as would be obvious to one having ordinary skill in this art may be made without departing from the scope of the invention as set forth in the claims appended hereto.

The invention claimed is:

1. A method of detecting interactions between species on a solid support and species in a liquid, comprising
    providing a solid support having at least two non-overlapping defined portions, wherein a first species is attached on at least one of said defined portions and at least one other defined portion is an area of the solid support where no interaction takes place, said other portion defining a reference area,
    wherein the detection of interactions comprises for each defined portion:
    exposing the defined portion to a liquid containing a second species, so as to cover the defined portion of the solid support;
    temporarily reducing the amount of said liquid being in contact with the defined portion, said reduction being carried out so that a reduced volume of said liquid remains in contact with said defined portion;
    performing a measurement of the defined portion covered with the temporarily reduced amount of liquid, said measurement being capable of detecting an interaction between said first and said second species;
    increasing the amount of liquid in contact with the defined portion so as to again expose the defined portion to said liquid containing a second species; and
    repeating the exposing to a liquid, reducing the amount of liquid, performing a measurement and increasing the amount of liquid;
    wherein the liquid in contact with the solid support is stirred; and
    wherein the non-overlapping defined portions are in contact with the liquid containing the second species while said exposing to a liquid, reducing the amount of liquid, performing a measurement and increasing the amount of liquid are conducted.

2. The method as claimed in claim 1, wherein the interactions on all defined areas are detected within 1 minute, and the detection of all interactions is time-resolved and repeated at least 15 times without interruption during at least 15 minutes in order determine the progress of the interaction over time.

3. The method as claimed in claim 1, wherein said temporary reduction of liquid comprises a reduction of the amount of liquid near at least one of said defined areas without changing the total amount of liquid in contact with said solid support.

4. The method as claimed in claim 1, wherein a difference between target and reference measurements is calculated.

5. The method as claimed in claim 1, wherein the exposing, reducing the amount of liquid, and measuring is repeated, and wherein the concentration of said second species is increased by a finite amount before exposing, reducing the amount of liquid, and measuring are repeated.

6. The method as claimed in claim 1, wherein the solid support is an essentially flat dish capable of holding a liquid confined within its boundaries.

7. The method as claimed in claim 1, wherein the reduction of the amount of liquid is achieved by orienting the support at an angle that deviates from the horizontal to provide an elevated part and a lower part of said support, such that the elevated part will be covered by less liquid than the lower part, and wherein the support is rotated at a predetermined speed of rotation.

8. A device for detecting interactions between a first species attached to a support and a second species present in a liquid, when said support and said liquid containing said second species are brought into contact, comprising:
    a solid support on which said first species can be attached in one or more non-overlapping defined areas;
    a detector capable of detecting an interaction between said first species attached to the solid support and said second species contained in said liquid;
    a mechanism adapted for stirring of the liquid in contact with the solid support and for temporarily reducing, in a defined area of said support, and in the course of a detection, the amount of liquid containing said second species with which said support is brought into contact, followed by increasing the amount of liquid being in contact with said defined area after said detection; wherein:
    at least one of the defined areas does not have said first species attached, so as to form a reference area for the detection; and
    said solid support is arranged such that it will not come in contact with any liquids other than said liquid containing said second species during the course of said detection.

9. Device as claimed in claim 8, wherein said solid support is an essentially flat circular dish capable of holding a liquid confined within its boundaries and wherein the mechanism adapted for stirring of the liquid in contact with the solid support and for temporarily reducing, in a defined area of said support, and in the course of a detection, the amount of liquid containing said second species with which said support is brought into contact comprises a rotating holder for said flat circular dish,
    said holder being oriented so that the support is maintained at an angle that deviates from the horizontal to provide an elevated part and a lower part of said support, such that the elevated part will be covered by less liquid than the lower part, and
    the device being provided with a motor to rotate the support at a predetermined speed of rotation.

10. The device as claimed in claim 8, wherein the detector is a scintillation detector, and wherein there is further provided an electronic counter device for counting the impulses from the detector, a control unit for adjusting and reporting the angular position of the support, and a computer for synchronizing scintillation counter output from the counter and the angular position of the support from the control unit.

* * * * *